United States Patent [19]

Lih-Sheng

[11] Patent Number: 4,862,876
[45] Date of Patent: Sep. 5, 1989

[54] DENTAL AND THROAT CLEANING SYSTEM

[76] Inventor: Ke Lih-Sheng, No. 14, Lane 561, Chong Shang Rd., Sha Lu Village, Taichong County, Taiwan, Taiwan

[21] Appl. No.: 233,607

[22] Filed: Aug. 18, 1988

[51] Int. Cl.⁴ .............................................. A61H 9/00
[52] U.S. Cl. .................................................... 128/66
[58] Field of Search ............... 128/66, 62 A; 433/80, 433/81, 85, 88

[56] References Cited

U.S. PATENT DOCUMENTS 2,757,668  8/1956  Meyer-Saladin ...................... 128/66
4,319,595  3/1982  Ulrich .................................... 128/66

FOREIGN PATENT DOCUMENTS 0663148  11/1987  Switzerland .......................... 433/80

Primary Examiner—John J. Wilson
Attorney, Agent, or Firm—Morton J. Rosenberg

[57] ABSTRACT

A dental and throat cleaning system is provided which includes an overall housing (10). Mounted within the housing (10) is a tooth cleaning water tank (20) and a throat cleaning water tank (40). The tooth cleaning water tank (20) is coupled to a water passage cylinder (30) through a water pump (23) mounted within the housing (10). A throat cleaning water tank (40) and associated heater (41) is coupled thorugh a spraying tube (43) to a spray conduit (50) which passes external to the housing (10). The spraying tube (43) passes adjacent a water pipe (44) which extends into water contained within the tooth cleaning water tank (20) and provides for cooling water to be mixed with the vapor in the spraying tube (43) for ejection through the spray conduit (50). An upper cover (60) covers the entire housing (10) to provide a compact package system. In this manner, both tooth cleaning and throat cleansing may be accomplished by one apparatus system through the system.

1 Claim, 5 Drawing Sheets

DENTAL AND THROAT CLEANING SYSTEM

BACKGROUND OF THE INVENTION

1. Field of the Invention

The subject dental and throat cleaning system relates to a device which allows for both cleaning the teeth and the throat of a user. In particular, this invention relates to a system wherein a tooth cleaning water tank and a throat cleaning water tank are both included within an overall housing. More in particular, this invention relates to a dental and throat cleaning system which provides for an external water passage cylinder coupled through a water pump to the tooth cleaning water tank for ejecting water under high pressure into the oral cavity of the user. Further, the subject invention relates to a dental and throat cleaning system wherein the throat cleaning water tank includes a heater which vaporizes water contained therein. More in particular, this invention directs itself to a dental and throat cleaning system where vaporized and heated water pass through a spraying tube and is mixed with cooling water passing from a water pipe extending into a tooth cleaning water tank for ejection through a spray conduit member into the throat area of the user. More in particular, this invention directs itself to a dental and throat cleaning system which may be used both for tooth cleaning as well as throat area cleansing. Further, this invention directs itself to a system which is simple however convenient and of low cost to manufacture for combining the functions of cleaning the teeth and the throat. Further, this invention directs itself to a system which requires a low volume space for use and is quite easy to operate by the user.

2. Prior Art

Both water ejecting systems and mist spray systems are known in some prior art. However, in many prior art systems, the functions of a tooth cleaning and a throat cleaning system are separate and distinct and not combined by interrelated element combination to provide a one package system which both cleans the teeth and the throat area of the user.

In various clinical dental centers or hospitals, dentists may have the occasion to clean teeth or the throat of a patient. Due to the fact that the teeth are cleaned by means of ejecting water and the throat is cleansed by means of spraying vapor, both of the operations are performed by different methods and using different equipment. Thus, two different systems and apparatuses are normally provided for respective application to the teeth or the throat and this has led to large space allocations and more expensive equipment.

SUMMARY OF THE INVENTION

A dental and throat cleaning system which includes an overall housing. A first water tank is located in a frontal portion of the housing for irrigating and cleansing teeth and surrounding gum tissue. The first water tank contains water and has an opening formed in the lower portion thereof. The water pump is placed in fluid communication with the opening in the lower portion of the first water tank. A water passage cylinder is fluidly coupled to the water pump with the water passage cylinder being adapted to receive a plurality of nozzle members for expelling water from the water passage cylinder at a predetermined velocity dependent upon the particular nozzle member being attached. A second water tank is located within a rear portion of the housing and has a thermal heater for heating water contained in the water tank. The second water tank has a pressure cover secured to the top of the second water tank and a vapor spray tube passes through the pressure cover. The spray tube has an end which is located adjacent a water pipe extending into the first water tank. The water pipe is coupled to an L-shaped plate member through a swivel joint to permit the water pipe to be rotated into and out of the first water tank. The rotation of the water pipe into and out of the first water tank allows the first water tank to be removed from the overall housing. A spray conduit is in communication with the end of the spray tube and the water pipe. The spray conduit passes external to the housing and is angularly adjustable. An upper cover is mounted over an upper portion of the housing for covering the first and second water tanks. The upper cover has an opening formed therethrough for insert of the spray conduit whereby the dental and throat cleaning system may be applied to both the tooth and throat area of a user.

DESCRIPTION OF THE PREFERRED EMBODIMENTS

Figure 1A:
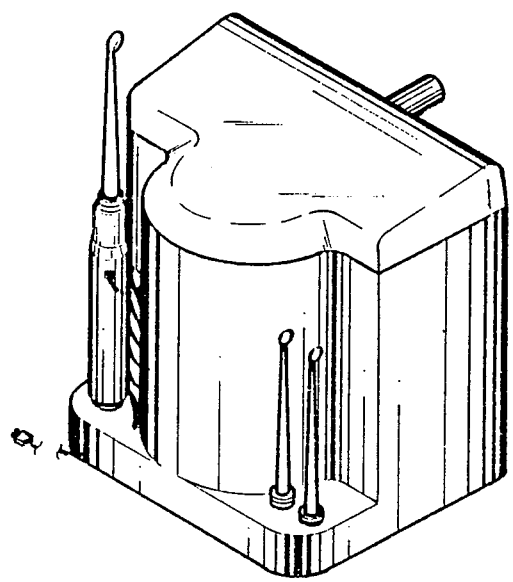
FIG. 1A is a perspective view of the overall dental and throat cleaning system.
Figure 1B:
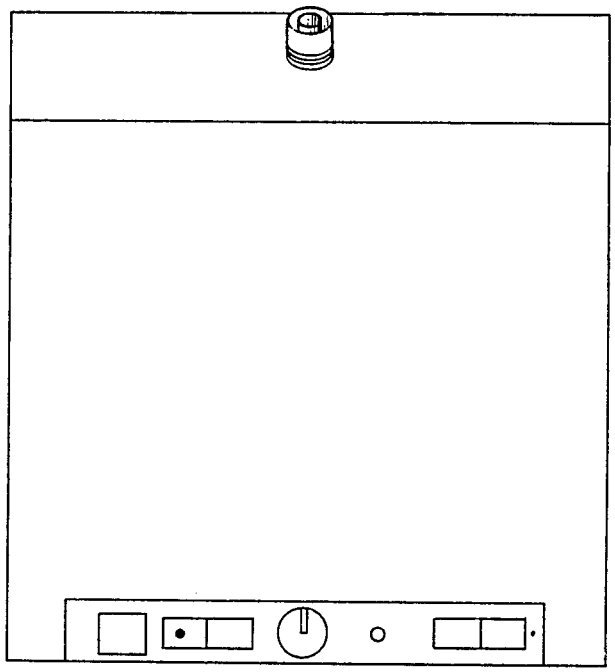
FIG. 1B is a frontal view of the dental and throat cleaning system of the subject invention showing the extension therefrom of the spray conduit member.
Figure 2:
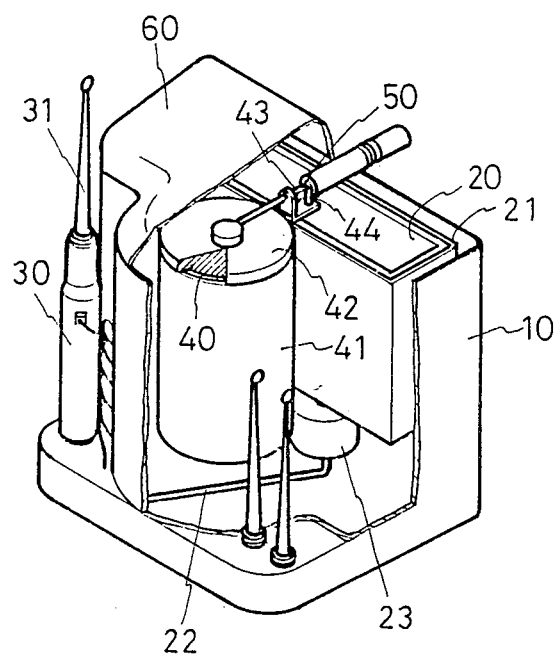
FIG. 2 is a perspective view partially cut away showing the internal elements of the dental and throat cleaning system of the subject invention.
Figure 3A:
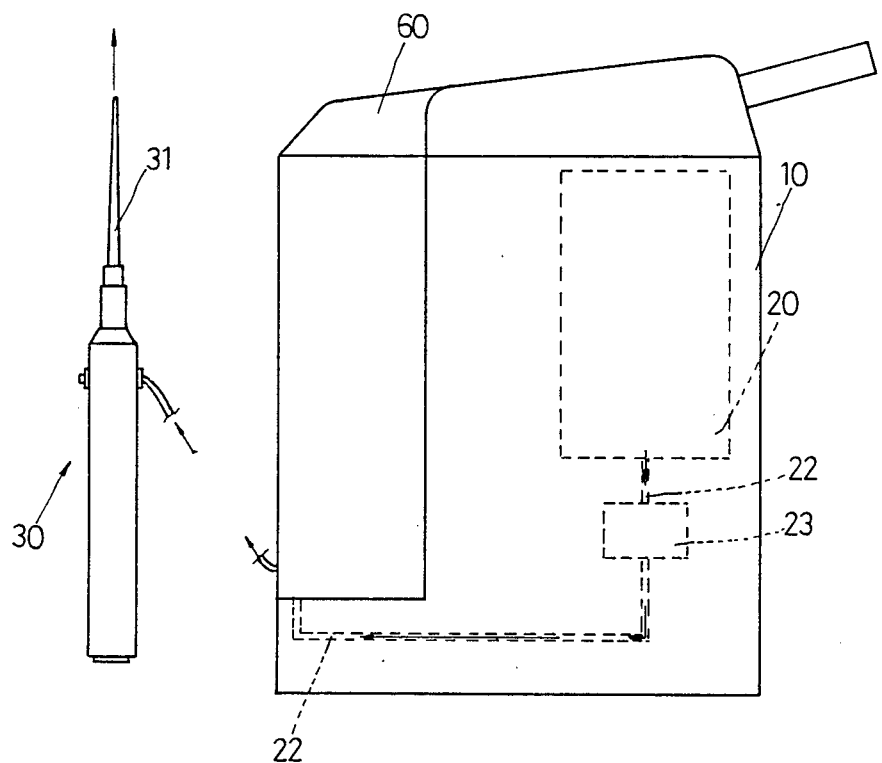
FIG. 3A is a side view partially cut away showing the water pump in its fluidly coupled state to the tooth cleaning water tank; and, FIG. 3B is a sectional view of the dental and throat cleaning system showing the internal components in operation.
Figure 3B:
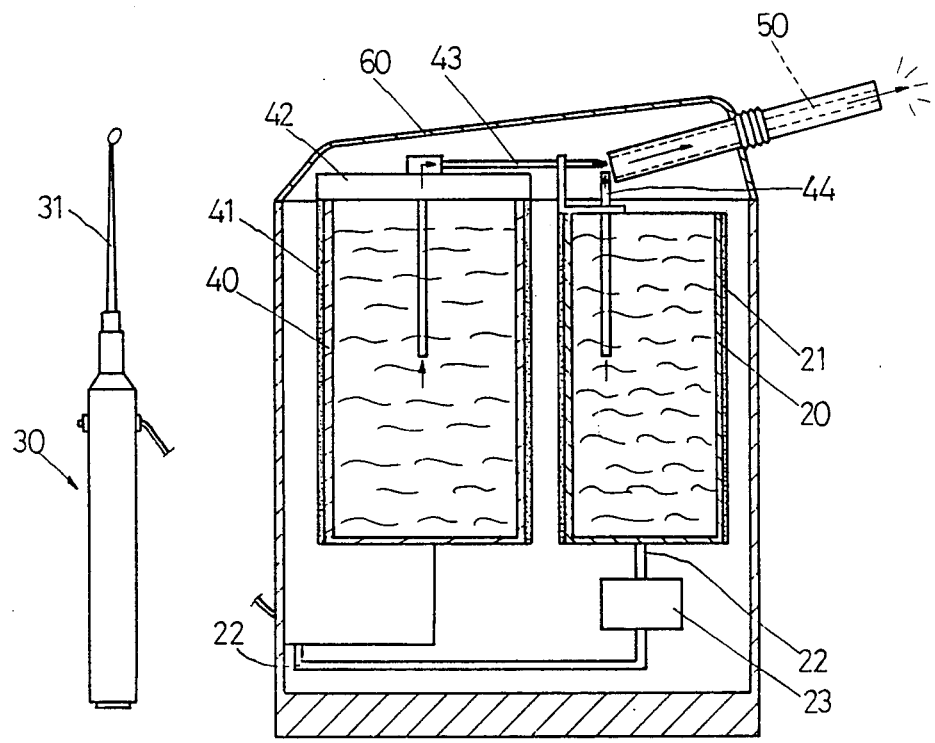

Referring now to FIGS. 1–3, there is shown a dental and throat cleaning system which includes overall housing 10 being mounted therein first or tooth cleaning water tank 20 for irrigating and cleansing teeth as well as surrounding gum tissue within the oral cavity of a user. As more clearly seen in FIG. 3B, first or tooth cleaning water tank 20 is adapted for receiving water therein. At a lower portion of first water tank 20 there is provided opening or entrance 21.

Water pump 23 is in fluid communication with the water contained within first water tank 20 at a lower end of housing 10. Water pump 23 is coupled to ejecting or water passage cylinder 30 through fluid conduit 22. Water passage cylinder 30 is merely one of a standard number of water type cylindrical members having a passage for water to be ejected into the oral cavity of a user. Water passage cylinder 30 is hand held by the handle and may be mounted on housing 10 as is shown in FIG. 2. Essentially, water passage cylinder 30 is manipulated by a user and includes nozzle member 31 for ejecting water into the oral cavity of the user. Nozzle member 31 may be mounted to water passage cylinder 30 by threaded securement or some like technique. As is seen in FIG. 2, a plurality of nozzle members 31 may be externally mounted to housing 10 to allow for differing orifice ejecting areas and provide for differing water velocities at the behest of the user.

Water pump 23 may be one of a number of commercially available type water pumps of the impeller type, such not being important to the inventive concept as herein described with the exception that such maintain a flow of water through fluid conduit 22.

Mounted within housing 10 is second water tank or throat cleansing water tank 40. The location of the throat cleansing water tank 40 is at the rear portion of housing 10 as is seen in FIG. 3B. Second water tank 40 is adapted to contain a quantity of water as is shown. Adjacent or even insertable within second water tank 40 is heater 41 which may be a resistance type encapsulated heater or some like heater well known in the art for heating water within second water tank 40.

Second water tank 40 includes pressure cover 42 for closing the top of second water tank 40.

Spraying tube 43 passes through pressure cover 42 as shown in FIG. 3B and is adapted to allow vapor to pass therethrough. Spraying tube member 43 passes through an L-shaped member which is mounted at an upper portion of housing 10 and has an end which passes adjacent an end of water pipe 44. Water pipe 44 is coupled to the L-shaped plate member through a swivel joint to allow rotation of water pipe 44 into and out of the water contained within first or tooth cleaning water tank 20.

As is seen in FIG. 3B, one end of water pipe 44 is adjacent an end of spraying tube 43 with both of the ends being in the neighborhood and in communication with spray conduit member 50. Spray conduit member 50 may be of a bellow shape and is adjustable to varying positions as is evident from the figure drawings. In this manner, spray conduit member 50 may be adjusted to a particular position to allow insert into the mouth of a user and thus allow spray combining with the water of first tank 20 to be impinged upon the throat area of the user.

Heated vapor passing through spraying tube 43 provides for a higher velocity passing the end of water pipe 44 which creates a low pressure zone and permits water to be passed along through spray conduit member 50 internal to the oral cavity of the user.

Upper cover 60 is mounted over an upper portion of housing 10 for covering first and second water tanks 20 and 40. Upper cover 60 has an opening formed therethrough for insert of spray conduit member 50 whereby the dental and throat cleaning system may be applied to both the tooth and throat area of a user for cleansing purposes.

As is standard in various prior art systems, it is clear that heater 41 may have a thermostatic control associated therewith to control the temperature of the heated water within second water tank 40. Additionally, the swivel joint provided for water pipe 44 on the L-shaped plate member allows swiveling of the water pipe 44 into a horizontal position and will allow removal of tooth cleaning or first water tank 20 from housing 10.

In operation, when teeth are being cleaned or alternatively the gums and tissues surrounding the teeth are being cleaned as is shown in FIG. 3A, an appropriate nozzle member 31 is threadedly secured to water passage cylinder or ejecting cylinder 30. The user may then insert nozzle member 31 into the oral cavity for cleansing the teeth. By a control switch (not shown) at the front of housing 10, water may go through opening 21 of tank 20 then through conduit 22 under force actuation by water tank 23. Finally, water is ejected from nozzle 31 for cleaning tartar on the teeth. Alternatively, when cleaning the throat as is shown in FIG. 3B, water from second water tank 40 is heated by heater 41 into a vaporized condition. The temperature of the water within second water tank 40 may be controlled by a thermostat. Vapor is ejected through spray tube member 43 at a relatively high pressure. Cool water in first tank 20 is sucked up due to the difference in pressure and forms a mist which is passed through spray conduit 50 in the form of a vapor mist for cleansing the throat area.

What is claimed is:

1. A dental and throat cleaning system comprising:
 (a) a housing;
 (b) a first water tank located in a frontal portion of said housing for irrigating and cleansing teeth and surrounding gum tissue, said first water tank containing water and having an opening formed in a lower portion thereof;
 (c) a water pump in fluid communication with said opening;
 (d) a water passage cylinder fluidly coupled to said water pump, said water passage cylinder being adapted to receive a plurality of nozzle members for expelling water from said water passage cylinder at a predetermined velocity;
 (e) a second water tank located within a rear portion of said housing having a thermal heater for heating water contained in said water tank, said second water tank having a pressure cover secured thereto and a vapor spray tube passing through said pressure cover, said spray tube having an end adjacent a water pipe extending into said first water tank, said water pipe coupled to an L-shaped plate member through a swivel joint to permit said water pipe to be rotated into and out of water contained in said first water tank;
 (f) a spray conduit in communication with said end of said spray tube and said water pipe, said spray conduit passing external said housing, said spray conduit being angularly adjustable; and,
 (g) an upper cover mounted over an upper portion of said housing for covering said first and second water tanks, said upper cover having an opening formed therethrough for insert of said spray conduit, whereby said dental and throat cleaning system may be applied to both the tooth and throat area of a user.

* * * * *